United States Patent
Tanthapanichakoon et al.

(10) Patent No.: US 7,955,610 B2
(45) Date of Patent: Jun. 7, 2011

(54) ANTIMICROBIAL COMPOSITION FOR TOPICAL APPLICATION AND A METHOD THEREOF

(75) Inventors: Wiwut Tanthapanichakoon, Pathumthani (TH); Uracha Rungsardthong, Pathumthani (TH); ML Sumarn Saraya, Bangkok (TH); Wasana Thaitae, Bangkok (TH)

(73) Assignees: National Science and Technology Development Agency, Prathumthani (TH); Nonami Science (Thailand) Co., Ltd., Bangkok (TH)

( * ) Notice: Subject to any disclaimer, the term of this patent is extended or adjusted under 35 U.S.C. 154(b) by 858 days.

(21) Appl. No.: 11/462,228

(22) Filed: Aug. 3, 2006

(65) Prior Publication Data

US 2007/0031461 A1     Feb. 8, 2007

(30) Foreign Application Priority Data

Aug. 4, 2005 (TH) ............................ 0501003619

(51) Int. Cl.
*A61K 33/00* (2006.01)
*A61K 33/12* (2006.01)
*A61K 33/40* (2006.01)

(52) U.S. Cl. ......... 424/405; 424/615; 424/617; 424/683

(58) Field of Classification Search ............ 424/615, 424/617, 683
See application file for complete search history.

(56) References Cited

U.S. PATENT DOCUMENTS

| | | | | |
|---|---|---|---|---|
| 5,520,918 A * | 5/1996 | Smith | ............ | 424/401 |
| 6,362,159 B1 * | 3/2002 | Aguadisch et al. | ............ | 512/4 |
| 7,037,511 B1 * | 5/2006 | Gers-Barlag et al. | ......... | 424/401 |
| 2003/0198616 A1 * | 10/2003 | Howard | .................. | 424/70.13 |
| 2004/0033246 A1 * | 2/2004 | Naru et al. | .................. | 424/401 |
| 2005/0175717 A1 * | 8/2005 | De La Mettrie et al. | ...... | 424/725 |

OTHER PUBLICATIONS

Kameyama,Tetsuya, et al., "Robust Science & Technology for Safe and Secure Life Space—Photocatalyst—," Public Relations Department, National Institute of Advanced Industrial Science and Technology (AIST), 8 pages. Retrieved at: http://www.aist.go.jp/aist_e/research_results/publications/pamphlet/today/photocatalyst_e.pdf. Metadata within the PDF file indicates "Created: Aug. 27, 2003" and "Modified: May 10, 2006." Screen capture of metadata screen attached as p. 9.

* cited by examiner

*Primary Examiner* — Sharmila G. Landau
*Assistant Examiner* — Kortney L Klinkel
(74) *Attorney, Agent, or Firm* — Baker & Daniels LLP

(57) ABSTRACT

The present invention provides an antimicrobial composition for topical application, preferably for treating acne, and a method for using the composition. The composition comprises a photocatalyst mixture comprising a photocatalyst, such as titanium dioxide, and sodium perborate, magnesium silicate, and citric acid. The photocatalyst mixture is in an amount effective as an antimicrobial under visible light. The method comprises applying the composition to a target area of the skin and exposing the area to visible light.

19 Claims, No Drawings

ANTIMICROBIAL COMPOSITION FOR TOPICAL APPLICATION AND A METHOD THEREOF

This application claims the benefit of Application No. 0501003619, filed in the Thai Patent Office on Aug. 4, 2005. Thai Application No. 0501003619 is hereby and herein incorporated by reference in its entirety.

FIELD OF THE INVENTION

The present invention relates to an antimicrobial composition particularly for use in cosmetics, and more particularly for facial application.

BACKGROUND

*Propionibacterium acnes* (*P. acnes*) is a gram positive anaerobic bacterium that is linked to many types of infection in humans. For example, *P. acnes* has been implicated in upper respiratory tract infections, skin and soft tissue infections, and is believed to be associated with over-production of sebum. Since *P. acnes* is a part of the normal flora of the skin, normally located in sebaceous follicles, it is therefore implicated in the pathogenesis of acne vulgaris, including associated inflammation caused by extracellular enzymes such as lipase and proteases. These enzymes hydrolyze sebum into free fatty acids, which also stimulate the inflammatory process. Chemotactic factors are released by this reaction, attracting neutrophils. As the follicular wall becomes inflamed, an erythematous papule appears at the skin's surface. With the increase of sebum production and bacterial colonization, the follicular unit ruptures, spilling its contents into the dermis. The inflow of neutrophils causes the formation of pustules. Continuation of severe inflammation leads to formation of nodules and subsequent cysts.

Acne vulgaris, or common acne, is a skin disorder of the pilosebaceous unit that generally develops in adolescence and adulthood. The term acne may refer to plugged pores (blackheads and whiteheads), pimples, and deeper lesions (cysts or nodules) that occur on the face, neck, chest, back, shoulders, and/or upper arms. While not a life-threatening condition, acne can be upsetting. Severe acne can also lead to serious and permanent scarring or disfigurement. Normally, acne can develop after one or more of the following occurrences: plugging of the hair follicle with abnormally cohesive desquamated cells, excess sebum production, rapid production of anaerobic skin-colonizing bacteria (including *P. acnes*) and release of inflammatory substances. Acne treatments involve various methods such as decreasing production, reducing *P. acnes* growth, normalizing skin shedding, and eliminating inflammation.

A variety of pharmaceutical products have been developed for the acne-treatment market. These products include antibiotics, vitamin A, and keratolytic agents. The effectiveness of these acne treatments vary from patient to patient, and adverse effects such as redness and hypersensitivity may occur. Therefore, new products capable of treating or preventing acnes, especially those caused by *P. acnes*, are needed.

Photocatalysts have been used for decomposition of harmful chemical substances in both air and water. Titanium dioxide is a semiconductor photocatalyst that is a crystaline form of anatase. It has an energy band gap equal to 3.2 eV. During the activation of $TiO_2$ with light at wavelengths lower than 385 nm, photon energy induces production of electron pairs on the surface of the titanium dioxide. These electron pairs can then further react with water, leading to the formation of free radicals, such as hydroxyl ions ($OH^-$) and superoxide ions ($O_2^-$). These free radicals possess strong oxidation power that can efficiently disassemble harmful organic chemical substances, ultimately yielding water and carbon dioxide.

Photocatalysts have been used to reduce the growth of bacteria in drinking water during purification processes and waste water treatment. Photocatalysts may be used to coat the interior and exterior walls of food packages to prevent growth of fungi and bacteria, or to eliminate foul odors. It is also known that photocatalyst coatings on air filters help inhibit bacterial contamination and eliminate odor, such as that from cigarette smoke. In addition, photocatalysts possess a bleaching property. Therefore, in dentistry, photocatalysts may be used as a cleaning agent for eliminating yellow stains from cigarettes, coffee and tartar.

However, a major disadvantage of photocatalysts is their inability to function without light, such as natural sunlight or 40 Watts black light.

One objective of the invention is to prepare an antimicrobial formulation for preventing or treating skin infections with little or no skin allergies or irritation. A more specific objective of the invention is to produce an antimicrobial composition that is effective under visible light for facial application.

SUMMARY OF THE INVENTION

The present invention comprises one or more of the following features or combinations thereof: a composition for topical application is provided comprising a photocatalyst that can scavenge organic substances and pathogens, including bacteria, under visible light. The composition includes a photocatalyst mixture comprising a photocatalyst (such as titanium dioxide), sodium perborate, magnesium silicate, and citric acid in an amount effective as an antimicrobial, particularly against *P. acnes*. The pH of the composition is adjusted to about pH 4 to about pH 6. Typically, the composition also comprises a pharmaceutically acceptable carrier, which may comprise water, oil, gel, cream, gum, suspension, and any combination thereof. The composition may be formulated into a solid, semi-solid or liquid form. In an exemplary embodiment, the composition contains titanium dioxide in an amount of about 0.0014% wt/v to about 0.0041% wt/v. The composition may also contain sodium perborate in an amount of about 0.1347% wt/v to about 0.4040% wt/v, magnesium silicate in an amount of about 0.0018% wt/v to about 0.0054% wt, and citric acid in an amount of about 0.1122% wt/v to about 0.3366% wt.

Additional features will become apparent to those skilled in the art upon consideration of the following detailed description of illustrative embodiments of the invention. The embodiments are not intended to be exhaustive or limit the invention to the precise form disclosed in the following detailed description. Rather, the embodiments are chosen and described so that others skilled in the art may utilize their teachings.

DETAILED DESCRIPTION OF THE INVENTION

A topical composition is provided that is effective against skin or facial bacteria and organic materials, with little or no skin allergy/irritation. The composition may be used to prevent or treat acne through its antimicrobial activity against *Propionibacterium acnes* (*P. acnes*). The composition includes a mixture which contains at least one photocatalyst. In one embodiment, the photocatalyst is titanium dioxide.

Other photocatalysts, such as nano silver, may also be used, either alone or in combination with titanium dioxide.

Other ingredients of the photocatalyst mixture include sodium perborate, magnesium silicate, and citric acid. These ingredients serve to enhance the photocatalytic activity of titanium dioxide when the composition is exposed to visible light. The proportion of the ingredients in the photocatalyst mixture may vary. For example, a ratio of about 1:about 100:about 1:about 80 of titanium dioxide:sodium perborate: magnesium silicate:citric acid, respectively, may be suitable. In one exemplary embodiment, the calculated ratio is 1:100: 1.33:83.3 of titanium dioxide: sodium perborate magnesium silicate:citric acid, respectively.

The photocatalyst mixture is made by first accurately measuring the proper amounts of each of the following ingredients: sodium perborate, magnesium silicate, citric acid and titanium dioxide. The correct amounts of sodium perborate and titanium dioxide are mixed together for about 15 minutes. (The mixing step may be performed in a mortar, or any suitable vessel.) If titanium dioxide is the photocatalyst used, the mixture becomes yellowish, indicating that a reaction between sodium perborate and titanium dioxide has occurred. Magnesium silicate and citric acid can then be added, and the mixing continues until a homogenous photocatalyst mixture is formed. One or more other photocatalysts can be added to the mixture. In one formulation, one gram of the photocatalyst mixture is dissolved in 100 ml of distilled water. The pH of the solution may be adjusted to a pH of about 4 to about 6. For example, the pH of 4.3 has been found to be suitable for use.

The concentration of the photocatalyst mixture in a solution or a final composition should be from 0.25 to 0.75% w/v. If the amount of the photocatalyst mixture is less than 0.25% w/v, the treatment's efficacy may not be satisfactory. Conversely, if the concentration of the photocatalyst mixture exceeds 0.75% w/v, adverse effects on the skin may occur. However, it is possible that one or more inert ingredients or anti-irritants may be added to help alleviate any adverse effects on the skin.

A preferred composition contains titanium dioxide in the amount of about 0.0014% wt/v to about 0.0041% wt/v. The sodium perborate is present in the amount of about 0.1347% wt/v to about 0.4040% wt/v. The magnesium silicate is present in the amount of about 0.0018% wt/v to about 0.0054% wt/v. In addition, the citric acid is present in the amount of about 0.1122% wt/v to about 0.3366% wt/v.

The composition may be further formulated using known methods to produce liquid, semi-solid or solid products. Traditional cosmetic or pharmaceutically acceptable carriers, such as water, oil, gel, cream, suspension, slurry, or a combination thereof may be added to produce skin cream or gel, ointment, liquid or bar soap, shampoo or conditioner or other suitable products. These products may be used on the acne-affected area to treat existing acne, or may be applied to normal skin areas that are prone to forming acne or to being infected by bacteria or other microorganisms.

Effective applications may vary depending on age, severity of infection, or part of the body affected. It is generally advisable that the target area is treated two or more times a day. Clinical study demonstrates a significant improvement in the appearance of facial acne lesions (both in the number of lesions and in their severity) after 28 days of twice-daily use of the composition.

EXAMPLE 1

Preparation of Titanium Dioxide Mixture 3 g of sodium perborate, 40 mg of magnesium silicate, 2.5 g of citric acid and 30 mg of titanium dioxide were weighted and kept separately. Then, the weighted amount of sodium perborate was mixed with the weighted amount of titanium dioxide in a mortar for about 15 minutes or until the color of the mixture turned yellowish. This color indicated a reaction between sodium perborate and titanium dioxide had occurred. The weighted amounts of magnesium silicate and citric acid were then added to the first mixture and mixed until a homogeneous photocatalyst mixture was obtained. To prepare a 1% w/v solution, one gram of the homogeneous photocatalyst mixture was dissolved in 100 ml of distilled water. The pH of the photocatalyst mixture solution was adjusted to a pH of 4 to 6.

EXAMPLE 2

Determination of Minimum Inhibitory Concentration (MIC) and Minimum Bactericidal Concentration (MBC) of the Photocatalyst Mixture

*Propionibacterium acnes* DMST14916 (*P. acnes*) was cultured in a brain heart agar (BHA) medium. The BHA medium was prepared by dissolving 52 g BHA in 1 liter of water and then adding glucose to reach final concentration of 1% glucose. The BHA medium was then sterilized by autoclaving at 121° C., at a pressure of 15 pounds/inch$^2$ for 15 minutes.

*P. acnes* was diluted with a brain heart infusion (BHI) broth to obtain a concentration equal to McFarland 0.5. The BHI broth was prepared by dissolving 37 g of BHI in 1 liter of water. Then glucose was added until a final concentration of 1% glucose was reached. The BHI was sterilized by autoclaving at 121° C., at a pressure of 15 pounds/inch$^2$ for 15 minutes.

Eleven test tubes were filled with BHI and varying amounts of the homogeneous photocatalyst mixture solution described in Example 1, and then *P. acnes* in various concentrations as shown in Table 2 was added to the test tubes. The tubes were then incubated at 37° C. in anaerobic conditions for at least 72 hours.

The clarity and turbidity of the samples were compared with a standard. The first tube was the clearest and the 10$^{th}$ tube was the most turbid. MIC was at a minimum concentration that could inhibit growth of bacteria.

To obtain MBC, which was at a minimum concentration that could destroy bacteria, the bacteria in all clear tubes were cultured in Petri dishes at 37° C. in anaerobic conditions for at least 72 hours. The results are shown in Table 1.

TABLE 1

MIC and MBC values of the *P. acnes* culture containing varying concentrations of titanium dioxide mixture

| Tube No. | BHI volume (ml) | A titanium dioxide mixture (ml) | Volume of P. acnes cell culture (ml) | A titanium dioxide mixture Appx. concentration (%) | MIC | MBC |
| --- | --- | --- | --- | --- | --- | --- |
| 1 | — | 1.98 (from a 1% mixture) | 0.02 | 1.0000 | clear | — |
| 2 | 1.98 | 1.98 (from a 1% mixture) | 0.02 | 1.0000 | clear | — |
| 3 | 1.98 | 1.98 (from tube 2) | 0.02 | 0.5000 | clear | — |

TABLE 1-continued

MIC and MBC values of the *P. acnes* culture containing varying concentrations of titanium dioxide mixture

| Tube No. | BHI volume (ml) | A titanium dioxide mixture (ml) | Volume of P. acnes cell culture (ml) | A titanium dioxide mixture Appx. concentration (%) | MIC | MBC |
|---|---|---|---|---|---|---|
| 4 | 1.98 | 1.98 (from tube 3) | 0.02 | 0.2500 | clear | — |
| 5 | 1.98 | 1.98 (from tube 4) | 0.02 | 0.1250 | turbid | n/a |
| 6 | 1.98 | 1.98 (from tube 5) | 0.02 | 0.0625 | turbid | n/a |
| 7 | 1.98 | 1.98 (from tube 6) | 0.02 | 0.0312 | turbid | n/a |
| 8 | 1.98 | 1.98 (from tube 7) | 0.02 | 0.0156 | turbid | n/a |
| 9 | 1.98 | 1.98 (from tube 8) | 0.02 | 0.0078 | turbid | n/a |
| 10 | 1.98 | — | 0.02 | — | turbid | n/a |
| 11 | 1.98 | 1.98 (from tube 9) | 0.02 | — | — | n/a | n/a = no test undertaken

The results demonstrated that all tubes with a titanium dioxide mixture concentration from 1% to 0.25% were clear, whereas from those with a titanium dioxide mixture concentration from 0.125% to 0.0078% were turbid. These results illustrated that MIC equals a concentration of a photocatalyst mixture of 0.25%. Further cultures of bacteria having 0.25% to 1.0% titanium dioxide mixture concentration on a Petri dish demonstrated that no bacteria growth can be observed, indicating that MBC equals to a concentration of the photocatalyst mixture at 0.25%. Therefore, it can be concluded that the minimum titanium dioxide mixture concentration that could inhibit and destroy the growth of bacteria is about 0.25% w/v.

EXAMPLE 3

Evaluation of Anti-microbial Activity

Propionibacterium acnes DMST14916 (*P. acnes*) was cultured using prepared brain heart agar (BHA*). The culture was incubated at 37° C. in anaerobic conditions for at least 72 hours. Separately, 15 ml of BHA was added into each Petri dish, and left until it became hardened. Afterward, 1.0 ml of a solution containing 1% w/v of the titanium dioxide mixture was mixed with BHA to reach a final volume of 4 ml. Therefore, the resulting concentration of the titanium dioxide-containing mixture was about 0.25%. This diluted solution was poured on the BHA medium surface in the Petri dish and let stand until it became a hard gel.

After the 72-hour incubation, the culture of *P. acnes* was diluted with the brain-heart infusion (BHI) broth until the turbidity standard of 0.5 on the McFarland scale was reached. Then, the culture was further serial diluted to $10^{-1}$, $10^{-2}$, $10^{-3}$, $10^{-4}$, $10^{-5}$, $10^{-6}$.

Subsequently, 0.1 ml of the $10^{-6}$ diluted culture was added onto each agar plate containing the titanium dioxide mixture, and incubated at 37° C. in anaerobic condition for at least 72 hours, after which, the growth of the bacteria (*P. acnes*) was determined. The result is shown in Table 2. The data represent 3 independent experiments and each was carried out in triplicate.

TABLE 2

Inhibitory efficiency of a titanium dioxide mixture on *P. acnes* growth

| | Colony forming unit/ml | | | | % |
|---|---|---|---|---|---|
| Sample | Experiment 1 | Experiment 2 | Experiment 3 | average | Bacterial Reduction |
| Titanium dioxide mixture | $1.3 \times 10^7$ | $2.7 \times 10^7$ | $3.3 \times 10^7$ | $2.4 \times 10^7$ | 93.81 |
| Positive control+ | — | — | — | — | 100 |
| Negative control++ | $92.3 \times 10^7$ | $16.3 \times 10^7$ | $7.7 \times 10^7$ | $38.8 \times 10^7$ | — |

+: Positive control is ClindaM (clindamycin 1% w/v)
—: No bacteria were observed.
++: Negative control composes of media and the cell culture with $10^{-6}$ concentration.

The results indicated that at the culture density of $10^{-6}$, 0.25% w/v of a titanium dioxide mixture can inhibit the growth of *P. acnes*, when compared with the control (no titanium dioxide mixture). The data show 95% confidence using independent sampled t-test; p-value was 0.020, which was less than 0.05.

EXAMPLE 4

Toxicity of the Titanium Dioxide Mixture on Human Skin

The toxicity of the mixture containing titanium dioxide was assayed by using indirect contact following ISO10993-5 and USP24. The third passage of human dermal fibroblasts was cultured in a suitable medium at 37° C. in a fully humidified, 5% $CO_2$ air atmosphere. About 2,000 cells were fed and cultured in 96-well plates for 48 hours. A 1% titanium dioxide mixture was mixed with a medium containing Dulbecco's Modified Eagle's Medium (DMEM), 10% fetal bovine serum and 2 mM L-glutamine in a ratio 1:2 (equal to 50% dilution), and was incubated for 24 hours. Afterward, the titanium dioxide was serial diluted into 8 concentrations as shown in Table 3. Each diluted mixture was incubated with the cell culture in Petri dishes for 24 hours prior to MTT assay for cell proliferation. To carry out MTT assay, 50 ml of tetrazolium dye was added in each well and incubated further for 4 hours. Tetrazolium dye was earlier prepared by dissolving 5 mg of the dye in one ml in phosphate buffer saline.

After discarding the medium in each well, 200 μl of DMSO and 25 μl Sorenzen's glycine buffer (pH 10.5) were added. Absorbance at 570 nm was measured by using a micro-titer plate reader. The results are shown in Table 3.

TABLE 3

The effect of a titanium dioxide mixture on percentage of cell survival

| A titanium dioxide mixture concentration (%) | % cells survival compared to control |
|---|---|
| 1.0000 | 53 ± 1 |
| 0.7500 | 68 ± 5 |
| 0.5000 | 84 ± 10 |

TABLE 3-continued

The effect of a titanium dioxide mixture on percentage of cell survival

| A titanium dioxide mixture concentration (%) | % cells survival compared to control |
|---|---|
| 0.2500 | 86 ± 3 |
| 0.1250 | 93 ± 7 |
| 0.1000 | 96 ± 5 |
| 0.0500 | 92 ± 3 |
| 0.0100 | 98 ± 1 |
| 0.0050 | 92 ± 1 |
| 0.0010 | 96 ± 1 |
| 0.0005 | 100 ± 3 |
| 0.0001 | 95 ± 1 |

From the results, the titanium dioxide mixture at 0.75 and 1% concentrations demonstrated high toxicity, whereas the concentrations lower than 0.75% did not result in any toxicity. Therefore, the mixture is safe for application on human skin, without toxicity, in recommended concentrations of 0.50% w/v or lower.

EXAMPLE 5

Clinical Study

The evaluation of the in vivo effect of titanium dioxide composition at 0.50% concentration of the mixture containing titanium dioxide was performed on 30 healthy Asian female subjects, aged between 18 and 25 years, each currently having acne lesions on the face. Each subject applied the titanium dioxide mixture solution on the facial acne lesions twice daily, in the morning and evening, over a 28 day-period. Two study designs were undertaken under the assumption that they were an open study, non-comparative test, and each subject served as her own reference. Cross-polarized digital photography, followed by a counting of the acne lesions and clinical evaluation of the facial skin appearance, was performed at day 0 and day 28. Consumer testing was performed by self-assessment questionnaire at day 28 in order to evaluate overall appraisal and attitude of the subjects towards the efficacy and tolerance of the product being tested. The results were expressed using all the subjects present at each examination time.

EXAMPLE 5.1

Numbers of Acne Lesions

After 28 days of use of the tested composition (with the titanium containing mixture), the mean values of acne lesion and standard deviations were calculated, as well as variations of the parameters relative to number of lesions at day 0. A decrease in the mean number of acne lesions was observed (Table 4), from an average of 23.4 down to 18.9 (mean variation=−19.4%). One-tailed paired student's t-test was employed to determine the significance of the results comparing between day 0 and day 28 with the level of significance at 5%. The results were positive since the photographic evaluation showed a significant decrease of the number of acne lesions after the treatment. This improvement was statistically significant compared to the baseline (T-value=$6.39 \times 10^{-04}$, $p < 1 \times 10^{-3}$). It should be noted that 70% (21 of 30) of the subjects from this study exhibited a reduction in the number of acne lesions on the face. The maximum decrease was observed for one subject, with about 85.7% decrease in the number of acne lesions on the face after 28 days of using the composition.

EXAMPLE 5.2

Blind Clinical Evaluation of the Photographs

Analysis of the photographs was performed as follows: pairs of pictures (same site for a given subject) were blindly presented to one observer who then tried to arrange them in chronological order of "before-after treatment". If the order was correctly arranged by the observer, then a score of +1 was allotted to the evaluation. If incorrect, a score of 0 was given. This photographic analysis gave a mean score of 0.73 (±0.45) (Table 5). The calculated 5% interval of confidence ranged from 0.57, up to 0.89. Since this 5% interval of confidence did not comprise the theoretical mean of 0.5 for a random arrangement in order, it is possible to conclude that a significant improvement in the facial appearance of acne lesions (both in the number of lesions and in their severity) had been observed after 28 days of using the composition.

TABLE 4

Counting of the acne lesion by cross-polarized digital photography

| | Raw values | | Variations (compared to baseline) | |
|---|---|---|---|---|
| Codes | T0 | T + 28 days | Difference | Variation (%/T0) |
| F0426 | 13 | 20 | 7 | 53.8% |
| F0654 | 23 | 13 | −10 | −43.5% |
| F0684 | 35 | 48 | 13 | 37.1% |
| F0833 | 17 | 12 | −5 | −29.4% |
| F0841 | 13 | 5 | −8 | −61.5% |
| F1164 | 31 | 33 | 2 | 6.5% |
| F1165 | 15 | 8 | −7 | −46.7% |
| F1192 | 24 | 17 | −7 | −29.2% |
| F1220 | 7 | 4 | −3 | −42.9% |
| F1400 | 12 | 13 | 1 | 8.3% |
| F1545 | 20 | 23 | 3 | 15.0% |
| F1696 | 31 | 26 | −5 | −16.1% |
| F1699 | 5 | 3 | −2 | −40.0% |
| F1757 | NE | Abs | Abs | Abs |
| F1762 | 33 | 38 | 5 | 15.2% |
| F1765 | 8 | 5 | −3 | −37.5% |
| F1768 | 25 | 15 | −10 | −40.0% |
| F1807 | 29 | 20 | −9 | −31.0% |
| F1879 | NE | Abs | Abs | Abs |
| F1880 | 14 | 8 | −6 | −42.9% |
| F1897 | 17 | 6 | −11 | −64.7% |
| F1898 | 43 | 22 | −21 | −48.8% |
| F1899 | 56 | 44 | −12 | −21.4% |
| F1900 | 6 | 6 | 0 | 0.0% |
| F1901 | 7 | 4 | −3 | −42.9% |
| F1902 | 5 | 6 | 1 | 20.0% |
| F1903 | 33 | 27 | −6 | −18.2% |
| F1904 | NE | Abs | Abs | Abs |
| F1906 | 24 | 13 | −11 | −45.8% |
| F1907 | 118 | 111 | −7 | −5.9% |
| F1908 | 8 | 8 | 0 | 0.0% |
| F1909 | 7 | 1 | −6 | −85.7% |
| F1910 | 23 | 7 | −16 | −69.6% |
| Mean | 23.4 | 18.9 | −4.5 | |
| S.D. | 21.8 | 21.4 | 7.0 | |
| Subjects | 30 | 30 | 30 | |

S.D.: Standard deviation
Abs: Absent
NE: Not exploited

TABLE 5

Blind arrangement of photographic evaluation

| Codes | Acne severity Score |
|---|---|
| F0426 | 1.0 |
| F0654 | 1.0 |
| F0684 | 1.0 |
| F0833 | 1.0 |
| F0841 | 1.0 |
| F1164 | 0.0 |
| F1165 | 1.0 |
| F1192 | 1.0 |
| F1220 | 1.0 |
| F1400 | 0.0 |
| F1545 | 0.0 |
| F1696 | 0.0 |
| F1699 | 1.0 |
| F1757 | Abs |
| F1762 | 0.0 |
| F1765 | 1.0 |
| F1768 | 1.0 |
| F1807 | 0.0 |
| F1879 | Abs |
| F1880 | 1.0 |
| F1897 | 1.0 |
| F1898 | 1.0 |
| F1899 | 1.0 |
| F1900 | 1.0 |
| F1901 | 1.0 |
| F1902 | 0.0 |
| F1903 | 1.0 |
| F1904 | Abs |
| F1906 | 0.0 |
| F1907 | 1.0 |
| F1908 | 1.0 |
| F1909 | 1.0 |
| F1910 | 1.0 |
| Mean | 0.73 |
| S.D. | 0.45 |
| Subjects | 30 |

EXAMPLE 5.3

Self-evaluation by Consumer Test

A descriptive analysis was undertaken by using Microsoft Excel software. The results were presented in the form of tables of numbers and frequencies of the answers for each proposal. The percentages were calculated by taking into consideration the total number of answers. In order to determine whether the differences in frequencies were significant, the percentages were compared by Chi-squared test with a threshold of significance at 5%. After 28 days of using the composition, most items related to the efficacy of the treatment were significantly recognized, with the exception of 2 claims for which the subjects neither agreed nor disagreed with. In particular: the product reduced the number of acne lesions for 80.0% of the subjects ($p<1\times10^{-5}$).

The product reduced the severity of the acne lesions for 76.7% of the subjects ($p<1\times10^{-4}$).

The anti-inflammatory effect was satisfactory in 73.3% of the cases ($p<1\times10^{-3}$).

TABLE 6

Results of the self-assessment by the subjects about the performances and in vivo efficacy of the titanium dioxide mixture after 28 days of twice daily application

| | % of agreement | P (Chi-2) | Significant at 5% |
|---|---|---|---|
| The product reduced the number of acne lesions | 80.0% | $6.14.10^{-6}$ | YES |
| The product reduced the severity of the acne lesions | 76.7% | $1.47.10^{-5}$ | YES |
| After 28 days of use of this product, the sebum excretion was reduced | 70.0% | $4.88.10^{-4}$ | YES |
| With this product, the skin was softer | 46.7% | $6.41.10^{-5}$ | YES* |
| The anti-inflammatory effect (decrease in skin's redness) of this product was satisfactory | 73.3% | $2.40.10^{-4}$ | YES |
| With this product, the skin was moisturized | 43.3% | $1.74.10^{-3}$ | YES* |
| This product did not dry or tighten the skin | 56.7% | $1.16.10^{-2}$ | YES |

YES*: significant difference in favor of "Neither agree nor disagree"

TABLE 7

Results of the self-assessment by the subjects about the texture and perception of the titanium dioxide mixture after 28 days of twice daily applications

| | % of agreement | P (Chi-2) | Significant at 5% |
|---|---|---|---|
| The tested product had a pleasant texture | 80.0% | $1.47.10^{-5}$ | YES |
| The product had a pleasant fragrance | 43.3% | $9.93.10^{-8}$ | YES* |
| The intensity of the product fragrance was just right | 73.3% | $6.91.10^{-13}$ | YES |
| This product was easy to use | 90.0% | $1.44.10^{-9}$ | YES |
| This product was pleasant to use | 80.0% | $6.14.10^{-6}$ | YES |
| At application of this product, the skin was moisturized | 46.7% | $6.41.10^{-6}$ | YES* |
| At application, the product did not tighten the skin | 50.0% | $2.35.1^{-2}$ | YES |
| At application, the product did not dry the skin | 56.7% | $3.18.10^{-3}$ | YES |

YES*: significant difference in favor of "Neither agree nor disagree"

What is claimed is:

1. A composition for topical application, comprising:
   a photocatalyst mixture comprising titanium dioxide, sodium perborate, magnesium silicate, and citric acid;
   at least one pharmaceutically acceptable carrier; and
   a pH range of about 4 to about 6;
   wherein the composition is effective as an antimicrobial under visible light and the photocatalyst mixture comprises titanium dioxide in an amount of about 0.0014% wt/v to about 0.0041% wt/v.

2. A composition for topical application, comprising:
a photocatalyst mixture comprising titanium dioxide, sodium perborate, magnesium silicate, and citric acid;
at least one pharmaceutically acceptable carrier; and
a pH range of about 4 to about 6;
wherein the composition is effective as an antimicrobial under visible light and the photocatalyst mixture comprises magnesium silicate in an amount of about 0.0018% wt/v to about 0.0054% wt/v.

3. A composition for topical application, comprising:
a photocatalyst mixture comprising titanium dioxide, sodium perborate, magnesium silicate, and citric acid;
at least one pharmaceutically acceptable carrier; and
a pH range of about 4 to about 6;
wherein the composition is effective as an antimicrobial under visible light and the photocatalyst mixture includes: titanium dioxide in an amount of about 0.0014% wt/v to about 0.0041% wt/v, sodium perborate in an amount of about 0.1347% wt/v to about 0.4040% wt/v, magnesium silicate in an amount of about 0.0018% wt/v to about 0.0054% wt/v, and citric acid in an amount of about 0.1122% wt/v to about 0.3366% wt/v.

4. A composition for topical application, comprising:
a photocatalyst mixture comprising titanium dioxide, sodium perborate, magnesium silicate, and citric acid;
at least one pharmaceutically acceptable carrier; and
a pH range of about 4 to about 6;
wherein the composition is effective as an antimicrobial under visible light and the photocatalyst mixture comprises titanium dioxide, sodium perborate, magnesium silicate, and citric acid in a proportion of about 1 to about 100 to about 1.3 to about 83.

5. A composition for topical application, comprising:
a photocatalyst mixture comprising titanium dioxide, sodium perborate, magnesium silicate, and citric acid;
at least one pharmaceutically acceptable carrier; and
a pH range of about 4 to about 6;
wherein the composition is effective as an antimicrobial under visible light and the photocatalyst mixture comprises titanium dioxide, sodium perborate, magnesium silicate, and citric acid in a proportion of 1:100:1.33:83.3.

6. A composition for topical application for treating acne, comprising:
a photocatalyst mixture in an amount effective for inhibiting growth of *Propionibacterium acnes*; and
a pharmaceutically acceptable carrier;
wherein the photocatalyst mixture comprises titanium dioxide, sodium perborate, magnesium silicate, and citric acid in a proportion of about 1 to about 100 to about 1.3 to about 83.

7. The composition of claim 6, wherein the pharmaceutically acceptable carrier comprises at least one of gum, gel, water, cream, oil, suspension, or a combination thereof.

8. The composition of claim 6, wherein the composition is one of a liquid, solid, or semi-solid.

9. The composition of claim 6, wherein the photocatalyst mixture comprises titanium dioxide in an amount of about 0.0014% wt/v to about 0.0041% wt/v.

10. The composition of claim 6, wherein the photocatalyst mixture comprises sodium perborate in an amount of about 0.1347% wt/v to about 0.4040% wt/v.

11. The composition of claim 6, wherein the photocatalyst mixture comprises magnesium silicate in an amount of about 0.0018% wt/v to about 0.0054% wt/v.

12. The composition of claim 6, wherein the photocatalyst mixture comprises citric acid in an amount of about 0.1122% wt/v to about 0.3366% wt/v.

13. The composition of claim 6, wherein the photocatalyst mixture comprises:
titanium dioxide in an amount of about 0.0014% wt/v to about 0.0041% wt/v;
sodium perborate in an amount of about 0.1347% wt/v to about 0.4040% wt/v;
magnesium silicate in an amount of about 0.0018% wt/v to about 0.0054% wt/v; and
citric acid in an amount of about 0.1122% wt/v to about 0.3366% wt/v.

14. The composition of claim 6, wherein the photocatalyst mixture comprises titanium dioxide, sodium perborate, magnesium silicate, and citric acid in a proportion of 1:100:1.33:83.3.

15. A composition for topical application, comprising:
a photocatalyst mixture comprising titanium dioxide in an amount of about 0.0014% wt/v to about 0.0041% wt/v, sodium perborate in an amount of about 0.1347% wt/v to about 0.4040% wt/v, magnesium silicate in an amount of about 0.0018% wt/v to about 0.0054% wt/v, and citric acid in an amount of about 0.1122% wt/v to about 0.3366% wt/v; and
at least one pharmaceutically acceptable carrier; and
wherein the composition is effective as an antimicrobial under visible light.

16. The composition of claim 15, wherein the pharmaceutically acceptable carrier comprises at least one of gum, water, cream, oil, suspension, or a combination thereof.

17. The composition of claim 15, wherein the composition is one of a liquid, solid, or semi-solid.

18. The composition of claim 15, wherein the photocatalyst mixture comprises titanium dioxide, sodium perborate, magnesium silicate, and citric acid in a proportion of about 1 to about 100 to about 1.3 to about 83.

19. The composition of claim 15, wherein the photocatalyst mixture comprises an amount effective for inhibiting the growth of *Propionibacterium acnes*.

* * * * *